US008423380B1

(12) United States Patent
Gelly (10) Patent No.: US 8,423,380 B1
(45) Date of Patent: Apr. 16, 2013

(54) METHOD AND SYSTEM FOR INTERACTIVE HEALTH REGIMEN ACCOUNTABILITY AND PATIENT MONITORING

(75) Inventor: George Gelly, Menlo Park, CA (US)

(73) Assignee: Intuit Inc., Mountain View, CA (US)

( * ) Notice: Subject to any disclaimer, the term of this patent is extended or adjusted under 35 U.S.C. 154(b) by 290 days.

(21) Appl. No.: 12/897,579

(22) Filed: Oct. 4, 2010

(51) Int. Cl.
*G06Q 50/00* (2006.01)

(52) U.S. Cl.
USPC .................................................. 705/2

(58) Field of Classification Search .................. 705/2
See application file for complete search history.

(56) References Cited

U.S. PATENT DOCUMENTS

| | | | | |
|---|---|---|---|---|
| 6,249,809 B1* | 6/2001 | Bro | ................ | 709/217 |
| 2005/0159977 A1* | 7/2005 | Green et al. | ................ | 705/2 |
| 2005/0182653 A1* | 8/2005 | Urban et al. | ................ | 705/2 |
| 2005/0283385 A1* | 12/2005 | Hunkeler et al. | ................ | 705/2 |
| 2011/0082711 A1* | 4/2011 | Poeze et al. | ................ | 705/3 |

* cited by examiner

*Primary Examiner* — Gerald J. O'Connor
*Assistant Examiner* — John Pauls
(74) *Attorney, Agent, or Firm* — McKay and Hodgson, LLP; Philip McKay; Sean P. Lewis (57) ABSTRACT

A method and system for providing an automated healthcare regimen monitoring and feedback system uses a healthcare regimen database that includes data related to healthcare regimen of various conditions using various healthcare related regimens. Once a healthcare related regimen is prescribed to a healthcare consumer by a healthcare service provider, the healthcare consumer provides contact information for their preferred method of contact and the healthcare consumer is then automatically contacted, via the selected form of contact, at intervals based on the data in the healthcare regimen database and/or entered additional information regarding the healthcare consumer, and/or the healthcare consumer's condition, and/or the prescribed healthcare regimen. Via this automatic contact, the healthcare consumer is provided reminders and other information regarding the prescribed healthcare regimen and, in some instances, asked for data and/or feedback.

20 Claims, 2 Drawing Sheets

FIG.1

METHOD AND SYSTEM FOR INTERACTIVE HEALTH REGIMEN ACCOUNTABILITY AND PATIENT MONITORING

BACKGROUND

Currently, when healthcare related regimens, such as drug prescriptions, physical therapy, or behavioral changes, are prescribed by a healthcare service provider to a healthcare consumer, the healthcare consumer is typically advised about potential desirable, and/or undesirable, reactions and expected results at the time the healthcare regimen is recommended. Then, typically, the healthcare consumer is advised to contact the healthcare service provider if any defined conditions/symptoms arise, or to check in at a predetermined later date. Currently, once this information is relayed to the healthcare consumer, the healthcare consumer is largely left on their own to comply with the prescribed regimen, monitor any results, watch for possible reactions and/or danger signs, and generally make sure the prescribed regimen is applied correctly and that the prescribed regimen is having the desired effect.

The current process described above often puts a significant burden on the healthcare consumer and leaves the healthcare consumer feeling out of touch with the healthcare service provider. As an example, consider a working parent whose child has an infection that requires antibiotics. Further assume that, as is the often case with antibiotics, the medicine must be administered three times a day on a full stomach. In addition, assume there is a possibility that the child will have an allergic reaction to the antibiotic. In this example, the parent must not only remember to make sure the antibiotic is administered three times a day, after the child has eaten, but the parent must also monitor the child for signs of an allergic reaction, which may be subtle, and/or subject to misinterpretation. In addition, the parent must monitor the child to determine if the medicine is having any positive effect. As a result the parent may either feel they have been more or less left to fend for themselves by the healthcare service provider or the parent may end up making numerous, and often unnecessary, calls and/or visits to the healthcare service provider as they try "play" doctor and comprehend what the results of their monitoring mean/indicate. This situation arises largely because, as noted, once the healthcare consumer has left the healthcare service providers office, they are, for the most part, out of contact with the healthcare service provider with no efficient feedback mechanism.

The situation described above not only often results in an undue level of healthcare consumer anxiety, but it can also represent a significant burden on healthcare service provider staff who currently must often answer numerous calls from concerned and/or confused healthcare consumers. In addition, the situation above can result in missed, or incorrect, applications of a prescribed healthcare regime, missed indications of ineffective or incorrect prescribed healthcare regimens, and/or other missed opportunities to cure. Clearly this is a less than ideal situation for both the healthcare consumers and the healthcare service providers.

SUMMARY

In accordance with one embodiment, a method and system for providing an automated healthcare regimen monitoring and feedback system includes a process for providing an automated healthcare regimen monitoring and feedback system whereby, in one embodiment, a healthcare regimen database is created that includes data related to healthcare regimen of various conditions using various healthcare related regimens. In one embodiment, once a healthcare related regimen is prescribed to a healthcare consumer by a healthcare service provider, the healthcare consumer is asked if they wish to participate in the healthcare regimen monitoring and feedback system. In one embodiment, once the healthcare consumer agrees to participate, the healthcare consumer provides contact information for their preferred method of contact, such as e-mail, text messaging/SMS, phone etc. In one embodiment, the healthcare service provider then associates/links the prescribed healthcare regimen with the healthcare consumer and, in one embodiment, enters additional information regarding the healthcare consumer, and/or the healthcare consumer's condition, and/or the prescribed healthcare regimen. In one embodiment, the healthcare consumer is then automatically contacted, via the selected form of contact, at intervals based on the data in the healthcare regimen database and/or the entered additional information regarding the healthcare consumer, and/or the healthcare consumer's condition, and/or the prescribed healthcare regimen. In one embodiment, through this automatic contact, the healthcare consumer is provided information regarding their prescribed healthcare regimen. In addition, in one embodiment, the healthcare consumer is asked to provide data and/or feedback based on, and/or specific to, the data in the healthcare regimen database, and/or the entered additional information/reminders regarding the healthcare consumer, and/or the healthcare consumer's condition, and/or the prescribed healthcare regimen. In one embodiment, the healthcare consumer is also provided more information regarding their prescribed healthcare regimen. In one embodiment, the data and/or feedback provided by multiple healthcare consumers is gathered and used to supplement the healthcare regimen database and/or to generally add to the set of all data related to a given prescribed healthcare regimen and/or condition/disease.

Using the method and system for providing an automated healthcare regimen monitoring and feedback system, discussed herein, a healthcare consumer can be automatically reminded/prompted to comply with a prescribed healthcare regimen, such as when to take a given prescribed dose of medicine, provided periodic information regarding what to expect at various phases of the healthcare regimen, and provided information regarding warning signs of allergic reactions or indications of ineffective healthcare regimen, all without having to directly contact the healthcare service provider. This, in turn, provides the healthcare consumer with a sense of being monitored and advised in an on-going manner through the entire prescribed healthcare regimen.

In addition, using the method and system for providing an automated healthcare regimen monitoring and feedback system, discussed herein, the healthcare consumer is also asked to provide specific data related to their experience with the prescribed regimen, often at various specific and/or critical stages of the healthcare regimen, and/or related to specific expected results or potential negative responses, throughout the entire prescribed regimen. Therefore, the healthcare service provider is provided relatively real-time and customized data regarding the healthcare consumer's experience and healing process so the healthcare consumer can more effectively monitor the healthcare consumer's progress. Consequently, using the method and system for providing an automated healthcare regimen monitoring and feedback system discussed herein, healthcare consumers are again benefited by increased monitoring and the healthcare service providers are benefited by receiving more data, and often more relevant data.

In addition, the data gathered by the healthcare service providers from the healthcare service consumers regarding the healthcare service consumers experience as various stages of the prescribed healthcare regime can be used to further refine the expected results data associated with a given healthcare regimen with respect to a given condition. Consequently, using the method and system for providing an automated healthcare regimen monitoring and feedback system, discussed herein, the entire population can be benefited by having access to more detailed and accurate data regarding a given healthcare regimen.

As discussed in more detail below, using the below embodiments, with little or no modification, there is considerable flexibility, adaptability, and opportunity for customization to meet the specific needs of various healthcare consumers under numerous circumstances.

Common reference numerals are used throughout the FIG.s and the detailed description to indicate like elements. One skilled in the art will readily recognize that the above FIG.s are examples and that other architectures, modes of operation, orders of operation and elements/functions can be provided and implemented without departing from the characteristics and features of the invention, as set forth in the claims below.

DETAILED DESCRIPTION

Embodiments will now be discussed with reference to the accompanying FIG.s, which depict one or more exemplary embodiments. Embodiments may be embodied in many different forms and should not be construed as limited to the embodiments set forth herein, shown in the FIG.s, and/or described below. Rather, these exemplary embodiments are provided to allow a complete disclosure that conveys the principles of the invention, as set forth in the claims, to those of skill in the art.

In accordance with one embodiment, a healthcare regimen database is created that includes data related to healthcare regimen of various conditions using various healthcare related regimens.

In one embodiment, the healthcare regimen database is a data storage device, a designated server system or computing system, or a designated portion of one or more server systems or computing systems, or a distributed database, or an external and/or portable hard drive. In one embodiment, the healthcare regimen database is a dedicated mass storage device implemented in software, hardware, or a combination of hardware and software. In one embodiment, healthcare regimen database is a web-based function.

In one embodiment, the healthcare regimen database includes data associated with various healthcare regimens such as, but not limited to: how often the healthcare regimen is to be administered, for instance, how often a pill or dose must be administered and/or how often an action is to be performed; results expected and/or expected symptoms at various stages of the administration of the healthcare regimen, for instance, how long, or how many, administrations of the prescribed healthcare regimen are needed before various results are expected; potential adverse reactions associated with the prescribed healthcare regimen; symptoms associated with adverse reactions to prescribed healthcare regimen; symptoms associated with various conditions that would require immediate action or indicate another healthcare regimen may be needed; conditions associated with administering the prescribed healthcare regimen, such as take only with, or without, food, what foods to avoid, etc.; and/or any other data related to a specific healthcare regimen and/or condition desired.

In one embodiment, a healthcare related regimen is prescribed to a healthcare consumer by a healthcare service provider. In one embodiment, the healthcare related regimen is prescribed to a healthcare consumer to treat a specific health condition. In one embodiment, once a healthcare related regimen is prescribed to a healthcare consumer by a healthcare service provider, the prescribed healthcare related regimen is added to the healthcare consumer's healthcare file and/or personal healthcare history, along with the associated health condition, and the healthcare consumer is asked if they wish to participate in the healthcare regimen monitoring and feedback system.

In one embodiment, once a healthcare consumer agrees to participate in the healthcare regimen monitoring and feedback system, the healthcare consumer provides contact information for their preferred method of contact, such as, but not limited to: e-mail; text messaging/SMS; mobile phone; traditional phone; PDA; mail; etc.

In one embodiment, the healthcare service provider then associates/links the prescribed healthcare regimen, the associated health condition, the healthcare consumer and contact information for the healthcare consumer, and the healthcare regimen database. In one embodiment, the healthcare service provider also enters additional information regarding the healthcare consumer, and/or the healthcare consumer's condition, and/or the prescribed healthcare regimen such as, but limited to: various data regarding the healthcare consumer such as age, weight, vital signs at the time of prescription, pre-existing conditions, health history, etc.; various parameters regarding the prescribed healthcare regimen, such as, but not limited to, dose, previous uses of the regimen by the healthcare consumer, etc.; any other drugs the healthcare consumer is known to use; and/or any other data regarding the healthcare consumer, and/or the healthcare consumer's condition, and/or the prescribed healthcare regimen deemed of consequence by the healthcare service provider.

In one embodiment, the healthcare consumer is then automatically contacted, via the selected form of contact, at intervals based on the data in the healthcare regimen database and/or the entered additional information regarding the healthcare consumer, and/or the healthcare consumer's condition, and/or the prescribed healthcare regimen. As part of this automatic contact, the healthcare consumer is provided information regarding their prescribed healthcare regimen.

For instance, in one embodiment, the healthcare consumer is then automatically contacted via e-mail, text message/SMS, phone, or mail and reminded to administer the prescribed healthcare regimen at the time the administration is due, e.g., the healthcare consumer is reminded to take his or her pill when it is due.

In one embodiment, the healthcare consumer is automatically contacted via e-mail, text message/SMS, phone, or mail and reminded to check various vital signs, such as temperature, blood sugar, etc., and, in one embodiment, provide this data to the healthcare service provider.

In one embodiment, the healthcare consumer is automatically contacted via e-mail, text message/SMS, phone, or mail and reminded to monitor various indications of an expected result of the prescribed healthcare regimen on, or about, the timeframe when the result is expected.

In one embodiment, the healthcare consumer is automatically contacted via e-mail, text message/SMS, phone, or mail and reminded to monitor signs of an adverse reaction to the prescribed healthcare regimen in a timely manner.

In one embodiment, the healthcare consumer is automatically asked to provide data and/or feedback based on, and/or specific to, the data in the healthcare regimen database, and/or the entered additional information regarding the healthcare consumer, and/or the healthcare consumer's condition, and/or the prescribed healthcare regimen. In one embodiment the healthcare consumer is also provided information regarding their prescribed healthcare regimen via e-mail, text message/SMS, phone, or mail.

For instance, in one embodiment, a healthcare consumer is asked to confirm compliance with an administration of the prescribed healthcare regimen on, or about, the time the administration of the prescribed healthcare regimen is due, e.g., the healthcare consumer is asked to confirm that they have taken their pill.

In one embodiment, the healthcare consumer is automatically asked to provide data and/or feedback regarding their personal observations regarding the progression of the healthcare regimen and/or any side effects he or she is experiencing at various stages of the healthcare regimen.

In one embodiment, the healthcare consumer is automatically given advice based on, and/or specific to, the data they supply as feedback and the data in the healthcare regimen database, and/or the entered additional information regarding the healthcare consumer, and/or the healthcare consumer's condition, and/or the prescribed healthcare regimen and provided information regarding their prescribed healthcare regimen via e-mail, text message/SMS, phone, or mail.

For instance, in one embodiment, if the data supplied by the healthcare consumer indicates that there is an allergic reaction, and/or that the healthcare regimen is ineffective, the healthcare consumer may be automatically advised to contact the healthcare service provider and/or another provider or service, such as a hospital or a 911 service.

In one embodiment, the data and/or feedback provided by multiple healthcare consumers is gathered and used to supplement/improve the healthcare regimen database and/or to generally add to data related to a given prescribed healthcare regimen and/or condition/disease.

Hardware System Architecture

FIG. 1 is a block diagram of an exemplary hardware architecture for implementing one embodiment of a system and method for providing an automated healthcare regimen monitoring and feedback system, such as exemplary process 200 (FIG. 2) discussed herein, that, returning to FIG. 1, includes: a provider system 100; a consumer system 150; a server system 120; and a database 170, all operatively coupled by a network 130.

Figure 1:
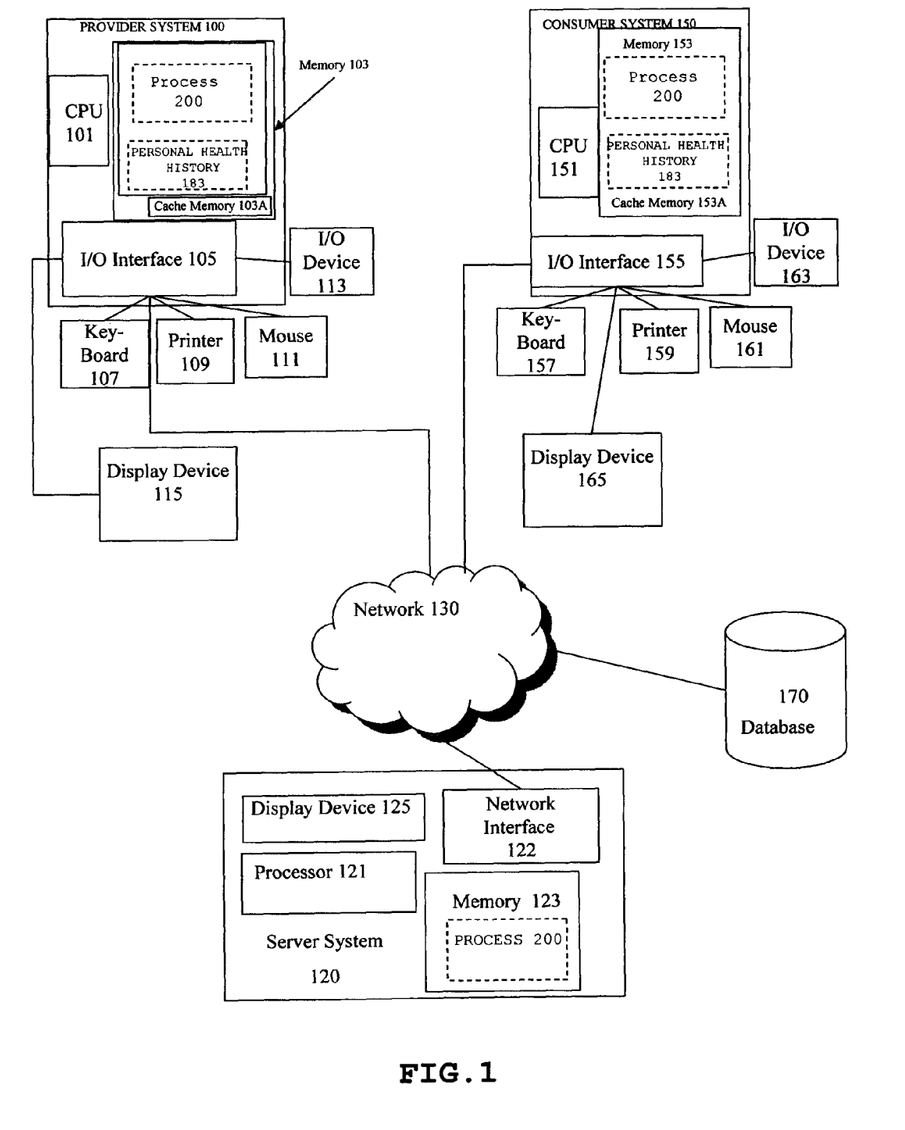
FIG. 1 is a block diagram of an exemplary hardware architecture for implementing one embodiment.

As seen in FIG. 1, provider system 100 typically includes a central processing unit (CPU) 101, an input/output (I/O) interface 105, and a memory system 103, including cache memory 103A. In one embodiment, memory system 103 includes all, or part of, a process for providing an automated healthcare regimen monitoring and feedback system 200 as discussed below.

In one embodiment, memory system 103 includes all, or part of, a personal health history 183 for one or more healthcare consumers such as, but not limited to, a digital personal health record for one or more healthcare consumers. In one embodiment, personal health history 183 is stored, in whole, or in part, in memory system 103, and is used by, or includes, as discussed below, a process for providing an automated healthcare regimen monitoring and feedback system, such as exemplary process 200 (FIG. 2) discussed below.

In one embodiment, provider system 100 is a computing system, desktop computing system, workstation, a two-way pager, a cellular telephone, a smart phone, a digital wireless telephone, a Personal Digital Assistant (PDA), a server computer, an Internet appliance, or any other device, or any desired combination of devices/systems.

As discussed in more detail below, in one embodiment, all, or part of, a process for providing an automated healthcare regimen monitoring and feedback system, and/or a personal health history, can be loaded, in whole, or in part, into provider system 100 for storage in memory system 103 and/or cache memory 103A.

Provider system 100 (FIG. 1) may further include standard user interface devices such as a keyboard 107, a mouse 111, a printer 109, and a display device 115, as well as, one or more standard input/output (I/O) devices 113, such as a compact disk (CD) or Digital Video Disc (DVD) drive, floppy disk drive, or other digital or waveform port, or other device capable of inputting data to, and outputting data from, provider system 100, whether available or known at the time of filing or as later developed. As discussed in more detail below, in one embodiment, a process for providing an automated healthcare regimen monitoring and feedback system and/or a personal health history are entered, in whole, or in part, into provider system 100 via I/O device 113, such as from a CD, DVD, floppy disk, portable hard drive, memory stick, download site, or other medium and/or computer program product as defined herein.

In one embodiment, provider system 100 is a computing system used and/or accessible by another computing system or physical device, such as consumer system 150.

As seen in FIG. 1, consumer system 150 typically includes a central processing unit (CPU) 151, an input/output (I/O) interface 155, and a memory system 153, including cache memory 153A. In one embodiment, memory system 153 includes all, or part of, a process for providing an automated healthcare regimen monitoring and feedback system 200 as discussed below.

In one embodiment, memory system 153 includes all, or part of, a personal health history 183 for one or more healthcare consumers such as, but not limited to, a digital personal health record for one or more healthcare consumers. In one embodiment, personal health history 183 is stored, in whole, or in part, in memory system 153, and is used by, or includes, as discussed below, a process for providing an automated healthcare regimen monitoring and feedback system, such as exemplary process 200 (FIG. 2) discussed below.

In one embodiment, consumer system 150, is a computing system such as, but not limited to, a desktop computing system; a workstation, a mobile phone, a two-way pager, a smart phone, a digital wireless telephone, a Personal Digital Assistant (PDA), a server computer, an Internet appliance, or any other device, or any desired combination of these devices, that includes components that can execute all, or part, of a process for providing an automated healthcare regimen monitoring and feedback system in accordance with at least one of the embodiments as described herein.

In one embodiment, similar to provider system 100, consumer system 150 typically includes a CPU 151, an input/output (I/O) interface 155, and a memory system 153, including cache memory 153A. Similar to provider system 100, consumer system 150 may further include standard user interface devices such as a keyboard 157, a mouse 161, a printer 159, and a display device 165, as well as, one or more standard input/output (I/O) devices 163, such as a compact disk (CD) or DVD drive, floppy disk drive, or other digital or waveform port, or other device capable of inputting data to, and outputting data from, consumer system 150, whether available or known at the time of filing or as later developed.

In one embodiment, consumer system 150 is a computing system used and/or accessible by another computing system, such as provider system 100.

Also shown in FIG. 1 is exemplary database 170. In one embodiment, database 170 is a healthcare regimen database as described herein. In one embodiment, database 170 is a data storage device, a designated server system or computing system, or a designated portion of one or more server systems or computing systems, such as systems 100, 150 and server system 120, or a distributed database, or an external and/or portable hard drive. In one embodiment, database 170 is a dedicated mass storage device implemented in software, hardware, or a combination of hardware and software. In one embodiment, database 170 is a web-based function. As discussed in more detail below, in one embodiment, database 170 is under the control of the healthcare consumer, and/or the healthcare consumer's agents, and/or a process for providing an automated healthcare regimen monitoring and feedback system, such as exemplary process 200 (FIG. 2), and/or a computing system implemented data management system, and/or a healthcare insurance provider.

In one embodiment, database 170 is used, controlled, and/or accessible by, a provider of and/or a system and processes for providing an automated healthcare regimen monitoring and feedback system, such as process for providing an automated healthcare regimen monitoring and feedback system 200 (FIG. 2), and includes data associated with various healthcare regimens such as, but not limited to: how often the healthcare regimen is to be administered, for instance how often a pill or dose must be administered and/or how often an action is to be performed; results expected and/or expected symptoms at various stages of the administration of the healthcare regimen, for instance how long, or how many, administrations of the prescribed healthcare regimen are needed before various results are expected; potential adverse reactions associated with the prescribed healthcare regimen; symptoms associated with adverse reactions to prescribed healthcare regimen; symptoms associated with various conditions that would require immediate action or indicate another healthcare regimen may be needed; conditions associated with administering the prescribed healthcare regimen, such as take only with, or without, food, what foods to avoid, etc.; and/or any other data related to a specific healthcare regimen and/or condition desired.

In one embodiment, provider system 100, consumer system 150, and database 170, are coupled to a server system 120, and/or each other, through network 130. In one embodiment, server system 120 typically includes a server system display device 125, a server system processor 121, a server system memory 123, and a server system network interface 122.

In one embodiment, server memory system 123 includes all, or part of, a process for providing an automated healthcare regimen monitoring and feedback system 200 as discussed below.

In one embodiment, provider system 100, consumer system 150, and database 170, are coupled through network 130. Network 130 can be any network or network system that is of interest to a healthcare consumer such as, a peer-to-peer network, a hybrid peer-to-peer network, a Local Area Network (LAN), a Wide Area Network (WAN), a public network, such as the Internet, a private network, a combination of different network types, or other wireless, wired, and/or a wireless and wired combination network capable of allowing communication between two or more computing systems, whether available or known at the time of filing or as later developed.

In one embodiment, provider system 100, consumer system 150, and database 170, and/or network 130 are part of a cloud computing environment.

Those of skill in the art will readily recognize that the components shown in FIG. 1, such as provider system 100, consumer system 150, database 170, server system 120, and their respective components, are shown for illustrative purposes only and that architectures with more or fewer components can implement, and benefit from, the invention. Moreover, one or more components of provider system 100, consumer system 150, database 170, and server system 120 may be located remotely from their respective system and accessed via network, as discussed herein. In addition, the particular type of, and configuration of, provider system 100, consumer system 150, database 170, and server system 120 are not relevant.

In one embodiment, a process for providing an automated healthcare regimen monitoring and feedback system, such as process for providing an automated healthcare regimen monitoring and feedback system 200 (FIG. 2), and/or a personal health history, such as personal health history 183, are computer applications or processes and/or data implemented and/or run and/or stored, in full, or in part, in, or on, a computer program product. Herein, a computer program product comprises a medium and/or I/O device configured to store or transport computer readable code, whether available or known at the time of filing or as later developed. Some examples of computer program products are CDs, DVDs, ROM cards, floppy discs, magnetic tapes, computer hard drives, portable hard drives, flash memory, volatile and non-volatile memory sticks, servers on a network, such as server system 120 of FIG. 1, and data transmitted over a network, such as network 130 of FIG. 1, or other media or process capable of delivering computer readable data representing computer readable code, whether available or known at the time of filing or as later developed. This medium may belong to a computing system, such as provider system 100 or consumer system 150 of FIG. 1, described above. However, in some embodiments, the medium also may be removable and/or remote from the computing system.

Process

Herein, the terms "healthcare consumer", "consumer", are used interchangeably to denote any person, party, or parties, who provide their information to, or for whom information is gathered by, a process for providing an automated healthcare regimen monitoring and feedback system, or for whom interaction with a process for providing an automated healthcare regimen monitoring and feedback system is performed, and/or an authorized agent of any person, party, or parties, who provide their information to, or for whom information is gathered by, a process for providing an automated healthcare regimen monitoring and feedback system, or for whom interaction with a process for providing an automated healthcare regimen monitoring and feedback system is performed.

Herein, the term "healthcare provider" and/or "healthcare service provider" denotes any individual person, persons, agencies, institutions, organizations, businesses, and/or other entities that provide medical healthcare regimen, medications, therapy, advice, and/or equipment. For example, herein, the term "healthcare provider" includes, but is not limited to: doctors; nurses; technicians; therapists; pharmacists; laboratories; counselors; alternative medicine practitioners; medical facilities; doctor's offices; hospitals; emergency rooms; clinics; urgent care centers; alternative medicine clinics/facilities; physical therapy clinics/facilities; and any other entity providing general and/or specialized healthcare regimen, assessment, maintenance, therapy, medication, and/or advice relating to all, or any portion of, a healthcare consumer's state of health, including but not limited to: general medical, specialized medical, surgical, dental, vision, psychological, and/or any other type of healthcare regimen, assessment, maintenance, therapy, medication, and/or advice.

Herein, the term "healthcare regimen" includes one or more medications and/or medication regimes; physical therapy; recommended dietary changes; lab work, recommended activity level changes; other lifestyle changes; and/or surgical procedures; and/or any prescribed and/or suggested regime, medication, treatment, activity, avoided activity, and/or program designed to improve, maintain, and/or slow the degradation of, a healthcare consumer's health and/or any general and/or specialized healthcare regimen, assessment, maintenance, therapy, medication, and/or advice relating to all, or any portion of, a healthcare consumer's state of health, including but not limited to: general medical, specialized medical, surgical, dental, vision, psychological, and/or any other type of healthcare regimen, assessment, maintenance, therapy, medication, and/or advice.

Herein, the terms "healthcare insurance plan", "healthcare benefit plan", "health insurance plan" and "health insurance program" are used interchangeably to denote any policy, program, means and/or mechanism whereby a healthcare consumer is provided healthcare benefits and/or healthcare services and/or entitlements to any form of healthcare.

As used herein, the term "computing system", includes, but is not limited to: a desktop computer; a portable computer; a workstation; a two-way pager; a cellular telephone; a smart phone; a digital wireless telephone; a Personal Digital Assistant (PDA); a media player, i.e., an MP3 player and/or other music and/or video player; a server computer; an Internet appliance; or any other device that includes components that can execute all, or part, of any one of the processes and/or operations as described herein. In addition, as used herein, the term computing system, can denote, but is not limited to, computing systems made up of multiple: computers; wireless devices; cellular telephones; digital telephones; two-way pagers; PDAs; media players; server computers; or any desired combination of these devices, that are coupled to perform the processes and/or operations as described herein.

As used herein, the term "computing system implemented data management system" includes, but is not limited to: computing system implemented accounting and/or invoicing systems, packages, programs, modules, or applications; financial management systems, packages, programs, modules, or applications; financial management systems, packages, programs, modules, or applications; computing system implemented banking systems, packages, programs, modules, or applications; computing system implemented personal and small business financial management systems, packages, programs, modules, or applications; computing system implemented business systems, packages, programs, modules, or applications; computing system implemented marketing device distribution systems, packages, programs, modules, or applications; computing system implemented financial institution financial management systems, packages, programs, modules, or applications; computing system implemented tax preparation systems, packages, programs, modules, or applications; computing system implemented business and/or point of sale systems, packages, programs, modules, or applications; computing system implemented healthcare management systems, packages, programs, modules, or applications and various other electronic data driven data management systems, packages, programs, modules, or applications, whether known at the time of filing or as developed later.

As used herein, the term "network" includes, but is not limited to, any network or network system such as, but not limited to, any one or more of the following, a peer-to-peer network, a hybrid peer-to-peer network, a Local Area Network (LAN), a Wide Area Network (WAN), a public network, such as the Internet, a private network, a cellular network, a combination of different network types, or other wireless, wired, and/or a wireless and wired combination network capable of allowing communication between two or more computing systems, whether available or known at the time of filing or as later developed.

As used herein, the term "database" includes, but is not limited to, any data storage mechanism known at the time of filing or as developed thereafter, such as, but not limited to, any one or more of the following: a data storage device; a designated server system or computing system, or a designated portion of one or more server systems or computing systems; a mobile computing system; a server system network; a distributed database; or an external and/or portable hard drive. Herein, the term "database" can refer to a dedicated mass storage device implemented in software, hardware, or a combination of hardware and software. Herein, the term "database" can refer to a web-based function. Herein, the term "database" can refer to any data storage means that is part of, or under the control of, any computing system, as discussed herein, known at the time of filing, or as developed thereafter.

In accordance with one embodiment, a method and system for providing an automated healthcare regimen monitoring and feedback system includes a process for providing an automated healthcare regimen monitoring and feedback system whereby, in one embodiment, a healthcare regimen database is created that includes data related to healthcare regimen of various conditions using various healthcare related regimens. In one embodiment, once a healthcare related regimen is prescribed to a healthcare consumer by a healthcare service provider, the healthcare consumer is asked if they wish to participate in the healthcare regimen monitoring and feedback system. In one embodiment, once the healthcare consumer agrees to participate, the healthcare consumer provides contact information for their preferred method of contact, such as e-mail, text messaging/SMS, phone etc. In one embodiment, the healthcare service provider then associates/links the prescribed healthcare regimen with the healthcare consumer and, in one embodiment, enters additional information regarding the healthcare consumer, and/or the healthcare consumer's condition, and/or the prescribed healthcare regimen. In one embodiment, the healthcare consumer is then automatically contacted, via the selected form of contact, at intervals based on the data in the healthcare regimen database and/or the entered additional information regarding the healthcare consumer, and/or the healthcare consumer's condition, and/or the prescribed healthcare regimen. In one embodiment, through this automatic contact, the healthcare consumer is provided information regarding their prescribed healthcare regimen. In addition, in one embodiment, the healthcare consumer is asked to provide data and/or feedback based on, and/or specific to, the data in the healthcare regimen database, and/or the entered additional information/reminders regarding the healthcare consumer, and/or the healthcare consumer's condition, and/or the prescribed healthcare regimen. In one embodiment, the healthcare consumer is also provided more information regarding their prescribed healthcare regimen. In one embodiment, the data and/or feedback provided by multiple healthcare consumers is gathered and used to supplement the healthcare regimen database and/or to generally add to the set of all data related to a given prescribed healthcare regimen and/or condition/disease.

Figure 2:
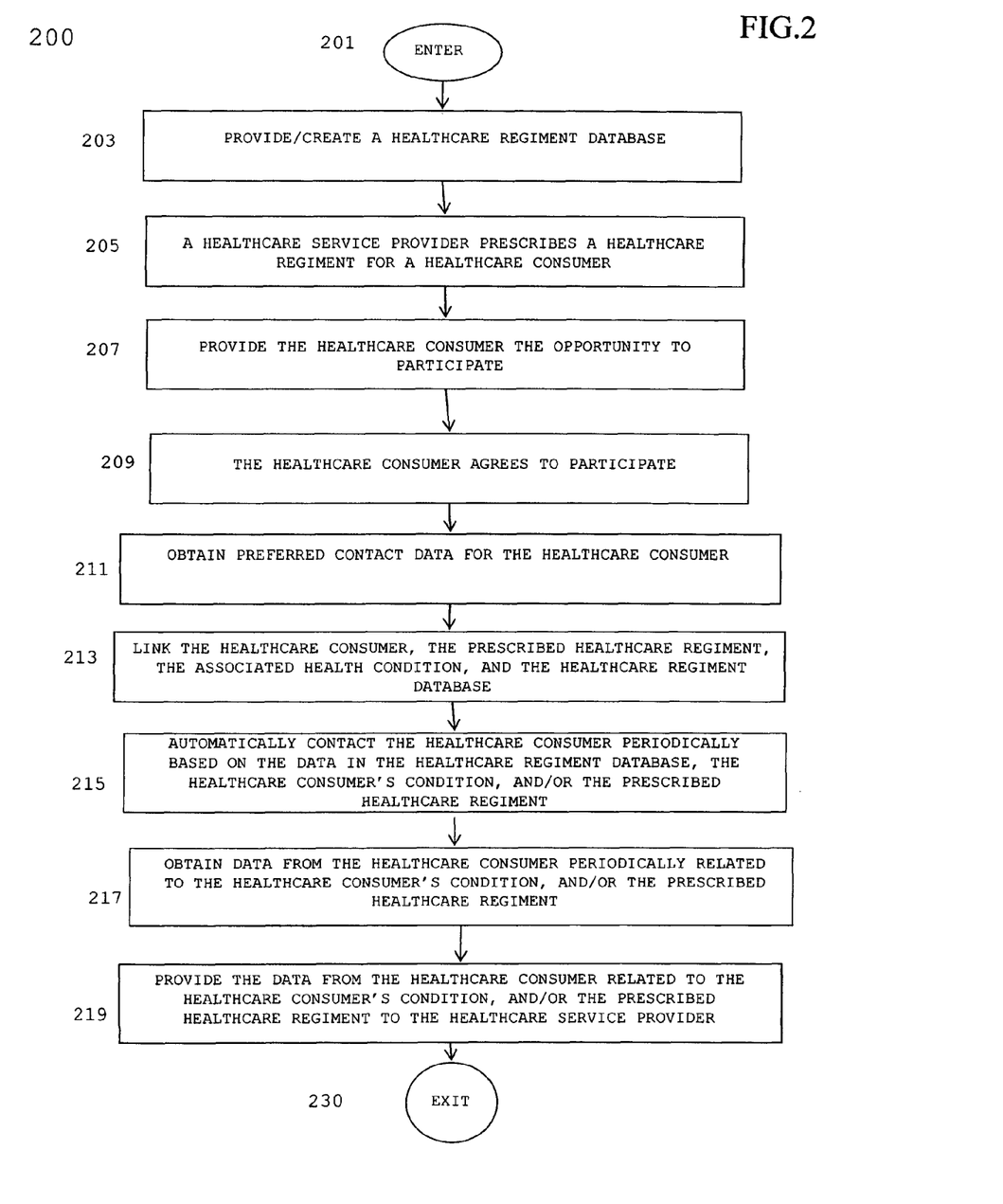
FIG. 2 is a flow chart depicting a process for providing an automated healthcare regimen monitoring and feedback system in accordance with one embodiment.

FIG. 2 a flow chart depicting a process for providing an automated healthcare regimen monitoring and feedback system 200 in accordance with one embodiment. Process for providing an automated healthcare regimen monitoring and feedback system 200 begins at ENTER OPERATION 201 of FIG. 2 and process flow proceeds to PROVIDE/CREATE A HEALTHCARE REGIMEN DATABASE OPERATION 203.

In one embodiment, at PROVIDE/CREATE A HEALTHCARE REGIMEN DATABASE OPERATION 203, a healthcare regimen database is created that includes data related to healthcare regimen of various conditions using various healthcare related regimens.

In one embodiment, at PROVIDE/CREATE A HEALTHCARE REGIMEN DATABASE OPERATION 203 the healthcare regimen database is a data storage device, such as database 170 of FIG. 1, and/or any designated server system or computing system, such as systems 100, 150 or 120 of FIG. 1, or a designated portion of one or more server systems or computing systems, or a distributed database, or an external and/or portable hard drive. In one embodiment, healthcare regimen database is a dedicated mass storage device implemented in software, hardware, or a combination of hardware and software. In one embodiment, healthcare regimen database is a web-based function.

Returning to FIG. 2, in one embodiment, the healthcare regimen database of PROVIDE/CREATE A HEALTHCARE REGIMEN DATABASE OPERATION 203 includes data associated with various healthcare regimens such as, but not limited to: how often the healthcare regimen is to be administered, for instance, how often a pill or dose must be administered and/or how often an action is to be performed; results expected and/or expected symptoms at various stages of the administration of the healthcare regimen, for instance, how long, or how many, administrations of the prescribed healthcare regimen are needed before various results are expected; potential adverse reactions associated with the prescribed healthcare regimen; symptoms associated with adverse reactions to prescribed healthcare regimen; symptoms associated with various conditions that would require immediate action or indicate another healthcare regimen may be needed; conditions associated with administering the prescribed healthcare regimen, such as take only with, or without, food, what foods to avoid, etc.; and/or any other data related to a specific healthcare regimen and/or condition desired.

In one embodiment, once a healthcare regimen database is created that includes data related to healthcare regimen of various conditions using various healthcare related regimens at PROVIDE/CREATE A HEALTHCARE REGIMEN DATABASE OPERATION 203, process flow proceeds to A HEALTHCARE SERVICE PROVIDER PRESCRIBES A HEALTHCARE REGIMEN FOR A HEALTHCARE CONSUMER OPERATION 205.

In one embodiment, at A HEALTHCARE SERVICE PROVIDER PRESCRIBES A HEALTHCARE REGIMEN FOR A HEALTHCARE CONSUMER OPERATION 205 a healthcare related regimen is prescribed to a healthcare consumer by a healthcare service provider.

In one embodiment, at A HEALTHCARE SERVICE PROVIDER PRESCRIBES A HEALTHCARE REGIMEN FOR A HEALTHCARE CONSUMER OPERATION 205 the healthcare related regimen is prescribed to the healthcare consumer to treat a specific health condition.

In one embodiment, once a healthcare related regimen is prescribed to a healthcare consumer by a healthcare service provider at A HEALTHCARE SERVICE PROVIDER PRESCRIBES A HEALTHCARE REGIMEN FOR A HEALTHCARE CONSUMER OPERATION 205, the prescribed healthcare related regimen is added to the healthcare consumer's healthcare file, along with the associated health condition, as personal health history data, such as personal health history 183 of FIG. 1.

Returning to FIG. 2, once a healthcare related regimen is prescribed to a healthcare consumer by a healthcare service provider at A HEALTHCARE SERVICE PROVIDER PRESCRIBES A HEALTHCARE REGIMEN FOR A HEALTHCARE CONSUMER OPERATION 205, process flow proceeds to PROVIDE THE HEALTHCARE CONSUMER THE OPPORTUNITY TO PARTICIPATE OPERATION 207.

In one embodiment, at PROVIDE THE HEALTHCARE CONSUMER THE OPPORTUNITY TO PARTICIPATE OPERATION 207 the healthcare consumer is asked if they wish to participate in, and/or is provided access to, the healthcare regimen monitoring and feedback system.

In one embodiment, at PROVIDE THE HEALTHCARE CONSUMER THE OPPORTUNITY TO PARTICIPATE OPERATION 207 the healthcare consumer is provided access to the healthcare regimen monitoring and feedback system via a website and/or web-based function and/or is provided log on information.

In one embodiment, once the healthcare consumer is asked if they wish to participate in, and/or is provided access to, the healthcare regimen monitoring and feedback system at PROVIDE THE HEALTHCARE CONSUMER THE OPPORTUNITY TO PARTICIPATE OPERATION 207, process flow proceeds to THE HEALTHCARE CONSUMER AGREES TO PARTICIPATE OPERATION 209.

In one embodiment, at THE HEALTHCARE CONSUMER AGREES TO PARTICIPATE OPERATION 209 the healthcare consumer agrees to participate in, and/or signs up/registers for, the healthcare regimen monitoring and feedback system.

In one embodiment, as part of the healthcare consumer's agreement to participate in the healthcare regimen monitoring and feedback system at THE HEALTHCARE CONSUMER AGREES TO PARTICIPATE OPERATION 209, the healthcare consumer agrees to waive defined privacy rights and to accept any other terms of the healthcare regimen monitoring and feedback system established by the provider of the healthcare regimen monitoring and feedback system, or other party, such as an insurance provider and/or the healthcare provider.

In one embodiment, as part of agreeing to participate in the healthcare regimen monitoring and feedback system, at THE HEALTHCARE CONSUMER AGREES TO PARTICIPATE OPERATION 209 the healthcare consumer agrees to allow various health related activities the healthcare consumer takes part in, and/or health related measurements/metrics, to be monitored and/or obtained and/or verified.

In one embodiment, examples of health related activities the healthcare consumer takes part in, and/or health related measurements/metrics, that are monitored and/or obtained and/or verified include, but are not limited to, one or more of the following: exercise levels and/or routines; diet; weight; heart rate; blood pressure; blood glucose levels; blood cholesterol levels; blood triglyceride levels; estimated calorie consumption; estimated calorie expenditure; alcohol consumption; drug use and/or drug use tests; participation in support groups; participation in educational groups; participation in therapy; participation in recommended regimes and/or activities; and/or or any other health related activity deemed of importance, and/or desirable, to monitor and/or measure.

In one embodiment, once the healthcare consumer agrees to participate in the healthcare regimen monitoring and feedback system at THE HEALTHCARE CONSUMER AGREES TO PARTICIPATE OPERATION 209, process flow proceeds to OBTAIN PREFERRED CONTACT DATA FOR THE HEALTHCARE CONSUMER OPERATION 211.

In one embodiment, at OBTAIN PREFERRED CONTACT DATA FOR THE HEALTHCARE CONSUMER OPERATION 211 the healthcare consumer provides contact information for their preferred method of contact, such as, but not limited to: e-mail; text messaging/SMS; mobile phone; traditional phone; PDA; mail; etc.

In one embodiment, once the healthcare consumer provides contact information for their preferred method of contact, such as, but not limited to: e-mail; text messaging/SMS; mobile phone; traditional phone; PDA; mail; etc. at OBTAIN PREFERRED CONTACT DATA FOR THE HEALTHCARE CONSUMER OPERATION 211, process flow proceeds to LINK THE HEALTHCARE CONSUMER, THE PRESCRIBED HEALTHCARE REGIMEN, THE ASSOCIATED HEALTH CONDITION, AND THE HEALTHCARE REGIMEN DATABASE OPERATION 213.

In one embodiment, at LINK THE HEALTHCARE CONSUMER, THE PRESCRIBED HEALTHCARE REGIMEN, THE ASSOCIATED HEALTH CONDITION, AND THE HEALTHCARE REGIMEN DATABASE OPERATION 213 the healthcare service provider then associates/links the prescribed healthcare regimen, the associated health condition, the healthcare consumer and contact information for the healthcare consumer, and the healthcare regimen database.

In one embodiment, at LINK THE HEALTHCARE CONSUMER, THE PRESCRIBED HEALTHCARE REGIMEN, THE ASSOCIATED HEALTH CONDITION, AND THE HEALTHCARE REGIMEN DATABASE OPERATION 213 the healthcare service provider also enters additional information regarding the healthcare consumer, and/or the healthcare consumer's condition, and/or the prescribed healthcare regimen such as, but limited to: various data regarding the healthcare consumer such as age, weight, vital signs at the time of prescription, pre-existing conditions, health history, etc.; various parameters regarding the prescribed healthcare regimen, such as, but not limited to, dose, previous uses of the regimen by the healthcare consumer, etc.; any other drugs the healthcare consumer is known to use; and/or any other data regarding the healthcare consumer, and/or the healthcare consumer's condition, and/or the prescribed healthcare regimen deemed to be of consequence by the healthcare service provider.

In one embodiment, once the healthcare service provider associates/links the prescribed healthcare regimen, the associated health condition, the healthcare consumer and contact information for the healthcare consumer, and the healthcare regimen database at LINK THE HEALTHCARE CONSUMER, THE PRESCRIBED HEALTHCARE REGIMEN, THE ASSOCIATED HEALTH CONDITION, AND THE HEALTHCARE REGIMEN DATABASE OPERATION 213, process flow proceeds to AUTOMATICALLY CONTACT THE HEALTHCARE CONSUMER PERIODICALLY BASED ON THE DATA IN THE HEALTHCARE REGIMEN DATABASE, THE HEALTHCARE CONSUMER'S CONDITION, AND/OR THE PRESCRIBED HEALTHCARE REGIMEN OPERATION 215.

In one embodiment, at AUTOMATICALLY CONTACT THE HEALTHCARE CONSUMER PERIODICALLY BASED ON THE DATA IN THE HEALTHCARE REGIMEN DATABASE, THE HEALTHCARE CONSUMER'S CONDITION, AND/OR THE PRESCRIBED HEALTHCARE REGIMEN OPERATION 215 the healthcare consumer is automatically contacted, via the selected form of contact, at intervals based on the data in the healthcare regimen database and/or the entered additional information regarding the healthcare consumer, and/or the healthcare consumer's condition, and/or the prescribed healthcare regimen and, as part of this automatic contact, the healthcare consumer is provided information regarding their prescribed healthcare regimen.

In one embodiment, at AUTOMATICALLY CONTACT THE HEALTHCARE CONSUMER PERIODICALLY BASED ON THE DATA IN THE HEALTHCARE REGIMEN DATABASE, THE HEALTHCARE CONSUMER'S CONDITION, AND/OR THE PRESCRIBED HEALTHCARE REGIMEN OPERATION 215 the healthcare consumer is automatically contacted, via the selected form of contact, at, or via, a consumer computing system, such as consumer system 100 of FIG. 1.

In one embodiment, at AUTOMATICALLY CONTACT THE HEALTHCARE CONSUMER PERIODICALLY BASED ON THE DATA IN THE HEALTHCARE REGIMEN DATABASE, THE HEALTHCARE CONSUMER'S CONDITION, AND/OR THE PRESCRIBED HEALTHCARE REGIMEN OPERATION 215 the healthcare consumer is automatically contacted, via the selected form of contact, using a computing system implemented data management system, and/or memory, and/or database under the control of the healthcare consumer, or another designated/certified party.

In one embodiment, at AUTOMATICALLY CONTACT THE HEALTHCARE CONSUMER PERIODICALLY BASED ON THE DATA IN THE HEALTHCARE REGIMEN DATABASE, THE HEALTHCARE CONSUMER'S CONDITION, AND/OR THE PRESCRIBED HEALTHCARE REGIMEN OPERATION 215 the healthcare consumer is automatically contacted, via the selected form of contact, by transmitting/transferring data to a healthcare consumer's personal health history, such as personal health history 183 of FIG. 1. In one embodiment the data in the healthcare consumer's personal health history is maintained by/in a computing system, and/or computing system implemented data management system, and/or memory, and/or database under the control of the healthcare consumer.

Returning to FIG. 2, in one embodiment, at AUTOMATICALLY CONTACT THE HEALTHCARE CONSUMER PERIODICALLY BASED ON THE DATA IN THE HEALTHCARE REGIMEN DATABASE, THE HEALTHCARE CONSUMER'S CONDITION, AND/OR THE PRESCRIBED HEALTHCARE REGIMEN OPERATION 215 the healthcare consumer is automatically contacted, via the selected form of contact, using a network or network system such as network 130 of FIG. 1, and/or any peer-to-peer network, a hybrid peer-to-peer network, a Local Area Network (LAN), a Wide Area Network (WAN), a public network, such as the Internet, a private network, a combination of different network types, or other wireless, wired, and/or a wireless and wired combination network capable of allowing communication between two or more computing systems and/or databases, whether available or known at the time of filing or as later developed.

Returning to FIG. 2, in one embodiment, at AUTOMATICALLY CONTACT THE HEALTHCARE CONSUMER PERIODICALLY BASED ON THE DATA IN THE HEALTHCARE REGIMEN DATABASE, THE HEALTHCARE CONSUMER'S CONDITION, AND/OR THE PRESCRIBED HEALTHCARE REGIMEN OPERATION 215 the healthcare consumer is automatically contacted, via the selected form of contact, by storing data representing the information on a database and then providing the healthcare consumer, or other designated party, access to the database. In one embodiment, the database is a data storage device, a designated server system or computing system, or a designated portion of one or more server systems or computing systems, or a distributed database, or an external and/or portable hard drive. In one embodiment, the database is a dedicated mass storage device implemented in software, hardware, or a combination of hardware and software. In one embodiment, the database is a web-based function.

Returning to FIG. 2, in one embodiment, at AUTOMATICALLY CONTACT THE HEALTHCARE CONSUMER PERIODICALLY BASED ON THE DATA IN THE HEALTHCARE REGIMEN DATABASE, THE HEALTHCARE CONSUMER'S CONDITION, AND/OR THE PRESCRIBED HEALTHCARE REGIMEN OPERATION 215 the healthcare consumer is automatically contacted, via the selected form of contact, via a computer program product as defined herein.

Returning to FIG. 2, in one embodiment, at AUTOMATICALLY CONTACT THE HEALTHCARE CONSUMER PERIODICALLY BASED ON THE DATA IN THE HEALTHCARE REGIMEN DATABASE, THE HEALTHCARE CONSUMER'S CONDITION, AND/OR THE PRESCRIBED HEALTHCARE REGIMEN OPERATION 215 the healthcare consumer is automatically contacted, via the selected form of contact, via any means, mechanism, method, process, procedure, or device for providing a healthcare consumer information and/or data, whether known at the time of filing or as developed thereafter.

Returning to FIG. 2, in one embodiment, at AUTOMATICALLY CONTACT THE HEALTHCARE CONSUMER PERIODICALLY BASED ON THE DATA IN THE HEALTHCARE REGIMEN DATABASE, THE HEALTHCARE CONSUMER'S CONDITION, AND/OR THE PRESCRIBED HEALTHCARE REGIMEN OPERATION 215 the healthcare consumer is automatically contacted via e-mail, text message/SMS, phone, or mail and reminded to administer the prescribed healthcare regimen at the time the administration is due, e.g., the healthcare consumer is reminded to take his or her pill when it is due.

In one embodiment, at AUTOMATICALLY CONTACT THE HEALTHCARE CONSUMER PERIODICALLY BASED ON THE DATA IN THE HEALTHCARE REGIMEN DATABASE, THE HEALTHCARE CONSUMER'S CONDITION, AND/OR THE PRESCRIBED HEALTHCARE REGIMEN OPERATION 215 the healthcare consumer is automatically contacted via e-mail, text message/SMS, phone, or mail and reminded to check various vital signs, such as temperature, blood sugar, etc., and, in one embodiment, provide this data to the healthcare service provider.

In one embodiment, at AUTOMATICALLY CONTACT THE HEALTHCARE CONSUMER PERIODICALLY BASED ON THE DATA IN THE HEALTHCARE REGIMEN DATABASE, THE HEALTHCARE CONSUMER'S CONDITION, AND/OR THE PRESCRIBED HEALTHCARE REGIMEN OPERATION 215 the healthcare consumer is automatically contacted via e-mail, text message/SMS, phone, or mail and reminded to monitor various indications of an expected result of the prescribed healthcare regimen on, or about, when that result is expected.

In one embodiment, at AUTOMATICALLY CONTACT THE HEALTHCARE CONSUMER PERIODICALLY BASED ON THE DATA IN THE HEALTHCARE REGIMEN DATABASE, THE HEALTHCARE CONSUMER'S CONDITION, AND/OR THE PRESCRIBED HEALTHCARE REGIMEN OPERATION 215 the healthcare consumer is automatically contacted via e-mail, text message/SMS, phone, or mail and reminded to monitor signs of an adverse reaction to the prescribed healthcare regimen in a timely manner.

In one embodiment, once the healthcare consumer is automatically contacted, via the selected form of contact, at intervals based on the data in the healthcare regimen database and/or the entered additional information regarding the healthcare consumer, and/or the healthcare consumer's condition, and/or the prescribed healthcare regimen and, as part of this automatic contact, the healthcare consumer is provided information regarding their prescribed healthcare regimen at AUTOMATICALLY CONTACT THE HEALTHCARE CONSUMER PERIODICALLY BASED ON THE DATA IN THE HEALTHCARE REGIMEN DATABASE, THE HEALTHCARE CONSUMER'S CONDITION, AND/OR THE PRESCRIBED HEALTHCARE REGIMEN OPERATION 215, process flow proceeds to OBTAIN DATA FROM THE HEALTHCARE CONSUMER PERIODICALLY RELATED TO THE HEALTHCARE CONSUMER'S CONDITION, AND/OR THE PRESCRIBED HEALTHCARE REGIMEN OPERATION 217.

In one embodiment, at OBTAIN DATA FROM THE HEALTHCARE CONSUMER PERIODICALLY RELATED TO THE HEALTHCARE CONSUMER'S CONDITION, AND/OR THE PRESCRIBED HEALTHCARE REGIMEN OPERATION 217 the healthcare consumer is automatically asked to provide data and/or feedback based on, and/or specific to, the data in the healthcare regimen database, and/or the entered additional information regarding the healthcare consumer, and/or the healthcare consumer's condition, and/or the prescribed healthcare regimen and, in one embodiment, the healthcare consumer is also provided information regarding their prescribed healthcare regimen via e-mail, text message/SMS, phone, or mail.

For instance, at OBTAIN DATA FROM THE HEALTHCARE CONSUMER PERIODICALLY RELATED TO THE HEALTHCARE CONSUMER'S CONDITION, AND/OR THE PRESCRIBED HEALTHCARE REGIMEN OPERATION 217 the healthcare consumer is asked to confirm compliance with an administration of the prescribed healthcare regimen on, or about the time the administration of the prescribed healthcare regimen is due, e.g., the healthcare consumer is asked to confirm that they have taken their pill.

In one embodiment, at OBTAIN DATA FROM THE HEALTHCARE CONSUMER PERIODICALLY RELATED TO THE HEALTHCARE CONSUMER'S CONDITION, AND/OR THE PRESCRIBED HEALTHCARE REGIMEN OPERATION 217 the healthcare consumer is automatically asked to provide data related to vital signs such as blood sugar levels, temperature, blood pressure etc.

In one embodiment, at OBTAIN DATA FROM THE HEALTHCARE CONSUMER PERIODICALLY RELATED TO THE HEALTHCARE CONSUMER'S CONDITION, AND/OR THE PRESCRIBED HEALTHCARE REGIMEN OPERATION 217 the healthcare consumer is automatically asked to provide data and/or feedback regarding an allergic reactions, and/or indicating that the healthcare regimen is ineffective, In one embodiment, at OBTAIN DATA FROM THE HEALTHCARE CONSUMER PERIODICALLY RELATED TO THE HEALTHCARE CONSUMER'S CONDITION, AND/OR THE PRESCRIBED HEALTHCARE REGIMEN OPERATION 217 the healthcare consumer is automatically asked to provide data and/or feedback regarding their personal feelings/observations regarding the progression of the healthcare regimen and/or any side effects he or she is experiencing at various stages of the healthcare regimen.

In one embodiment, at OBTAIN DATA FROM THE HEALTHCARE CONSUMER PERIODICALLY RELATED TO THE HEALTHCARE CONSUMER'S CONDITION, AND/OR THE PRESCRIBED HEALTHCARE REGIMEN OPERATION 217 the healthcare consumer is automatically asked to provide data and/or feedback regarding potential allergic reactions, and/or indicating that the healthcare regimen is ineffective.

In one embodiment, at OBTAIN DATA FROM THE HEALTHCARE CONSUMER PERIODICALLY RELATED TO THE HEALTHCARE CONSUMER'S CONDITION, AND/OR THE PRESCRIBED HEALTHCARE REGIMEN OPERATION 217 the healthcare consumer provides data/feedback via a consumer computing system, such as consumer system 100 of FIG. 1 and/or a provider system such as provider system 150 of FIG. 1.

Returning to FIG. 2, In one embodiment, at OBTAIN DATA FROM THE HEALTHCARE CONSUMER PERIODICALLY RELATED TO THE HEALTHCARE CONSUMER'S CONDITION, AND/OR THE PRESCRIBED HEALTHCARE REGIMEN OPERATION 217 the healthcare consumer provides data/feedback using a computing system implemented data management system, and/or memory, and/or database under the control of the healthcare consumer, or another designated/certified party.

In one embodiment, at OBTAIN DATA FROM THE HEALTHCARE CONSUMER PERIODICALLY RELATED TO THE HEALTHCARE CONSUMER'S CONDITION, AND/OR THE PRESCRIBED HEALTHCARE REGIMEN OPERATION 217 the healthcare consumer provides data/feedback by transmitting/transferring data to a healthcare consumer's personal health history, such as personal health history 183 of FIG. 1. In one embodiment the data in the healthcare consumer's personal health history is maintained by/in a computing system, and/or computing system implemented data management system, and/or memory, and/or database under the control of the healthcare consumer.

Returning to FIG. 2, In one embodiment, at OBTAIN DATA FROM THE HEALTHCARE CONSUMER PERIODICALLY RELATED TO THE HEALTHCARE CONSUMER'S CONDITION, AND/OR THE PRESCRIBED HEALTHCARE REGIMEN OPERATION 217 the healthcare consumer provides data/feedback using a network or network system such as network 130 of FIG. 1, and/or any peer-to-peer network, a hybrid peer-to-peer network, a Local Area Network (LAN), a Wide Area Network (WAN), a public network, such as the Internet, a private network, a combination of different network types, or other wireless, wired, and/or a wireless and wired combination network capable of allowing communication between two or more computing systems and/or databases, whether available or known at the time of filing or as later developed.

Returning to FIG. 2, in one embodiment, at OBTAIN DATA FROM THE HEALTHCARE CONSUMER PERIODICALLY RELATED TO THE HEALTHCARE CONSUMER'S CONDITION, AND/OR THE PRESCRIBED HEALTHCARE REGIMEN OPERATION 217 the healthcare consumer provides data/feedback by storing data representing the information on a database and then providing the healthcare consumer, or other designated party, access to the database. In one embodiment, the database is a data storage device, a designated server system or computing system, or a designated portion of one or more server systems or computing systems, or a distributed database, or an external and/or portable hard drive. In one embodiment, the database is a dedicated mass storage device implemented in software, hardware, or a combination of hardware and software. In one embodiment, the database is a web-based function.

Returning to FIG. 2, In one embodiment, at OBTAIN DATA FROM THE HEALTHCARE CONSUMER PERIODICALLY RELATED TO THE HEALTHCARE CONSUMER'S CONDITION, AND/OR THE PRESCRIBED HEALTHCARE REGIMEN OPERATION 217 the healthcare consumer provides data/feedback via a computer program product as defined herein.

In one embodiment, at OBTAIN DATA FROM THE HEALTHCARE CONSUMER PERIODICALLY RELATED TO THE HEALTHCARE CONSUMER'S CONDITION, AND/OR THE PRESCRIBED HEALTHCARE REGIMEN OPERATION 217 the healthcare consumer provides data/feedback via any means, mechanism, method, process, procedure, or device for providing a healthcare consumer information and/or data, whether known at the time of filing or as developed thereafter.

In one embodiment, once the healthcare consumer is automatically asked to provide data and/or feedback based on, and/or specific to, the data in the healthcare regimen database, and/or the entered additional information regarding the healthcare consumer, and/or the healthcare consumer's condition, and/or the prescribed healthcare regimen and, in one embodiment, the healthcare consumer is also provided information regarding their prescribed healthcare at OBTAIN DATA FROM THE HEALTHCARE CONSUMER PERIODICALLY RELATED TO THE HEALTHCARE CONSUMER'S CONDITION, AND/OR THE PRESCRIBED HEALTHCARE REGIMEN OPERATION 217, process flow proceeds to PROVIDE THE DATA FROM THE HEALTHCARE CONSUMER RELATED TO THE HEALTHCARE CONSUMER'S CONDITION, AND/OR THE PRESCRIBED HEALTHCARE REGIMEN TO THE HEALTHCARE SERVICE PROVIDER 219.

In one embodiment, at PROVIDE THE DATA FROM THE HEALTHCARE CONSUMER RELATED TO THE HEALTHCARE CONSUMER'S CONDITION, AND/OR THE PRESCRIBED HEALTHCARE REGIMEN TO THE HEALTHCARE SERVICE PROVIDER 219 the data and/or feedback of OBTAIN DATA FROM THE HEALTHCARE CONSUMER PERIODICALLY RELATED TO THE HEALTHCARE CONSUMER'S CONDITION, AND/OR THE PRESCRIBED HEALTHCARE REGIMEN OPERATION 217 is provided to the healthcare service provider.

In one embodiment, at PROVIDE THE DATA FROM THE HEALTHCARE CONSUMER RELATED TO THE HEALTHCARE CONSUMER'S CONDITION, AND/OR THE PRESCRIBED HEALTHCARE REGIMEN TO THE HEALTHCARE SERVICE PROVIDER 219 the data and/or feedback of OBTAIN DATA FROM THE HEALTHCARE CONSUMER PERIODICALLY RELATED TO THE HEALTHCARE CONSUMER'S CONDITION, AND/OR THE PRESCRIBED HEALTHCARE REGIMEN OPERATION 217 is provided to the healthcare service provider via a consumer computing system, such as consumer system 100 of FIG. 1 and/or a provider system such as provider system 150 of FIG. 1.

Returning to FIG. 2, in one embodiment, at PROVIDE THE DATA FROM THE HEALTHCARE CONSUMER RELATED TO THE HEALTHCARE CONSUMER'S CONDITION, AND/OR THE PRESCRIBED HEALTHCARE REGIMEN TO THE HEALTHCARE SERVICE PROVIDER 219 the data and/or feedback of OBTAIN DATA FROM THE HEALTHCARE CONSUMER PERIODICALLY RELATED TO THE HEALTHCARE CONSUMER'S CONDITION, AND/OR THE PRESCRIBED HEALTHCARE REGIMEN OPERATION 217 is provided to the healthcare service provider using a computing system implemented data management system, and/or memory, and/or database under the control of the healthcare service provider, or another designated/certified party.

In one embodiment, at PROVIDE THE DATA FROM THE HEALTHCARE CONSUMER RELATED TO THE HEALTHCARE CONSUMER'S CONDITION, AND/OR THE PRESCRIBED HEALTHCARE REGIMEN TO THE HEALTHCARE SERVICE PROVIDER 219 the data and/or feedback of OBTAIN DATA FROM THE HEALTHCARE CONSUMER PERIODICALLY RELATED TO THE HEALTHCARE CONSUMER'S CONDITION, AND/OR THE PRESCRIBED HEALTHCARE REGIMEN OPERATION 217 is provided to the healthcare service provider by transmitting/transferring data to a healthcare consumer's personal health history, such as personal health history 183 of FIG. 1. In one embodiment the data in the healthcare consumer's personal health history is maintained by/in a computing system, and/or computing system implemented data management system, and/or memory, and/or database under the control of the healthcare service provider.

Returning to FIG. 2, in one embodiment, at PROVIDE THE DATA FROM THE HEALTHCARE CONSUMER RELATED TO THE HEALTHCARE CONSUMER'S CONDITION, AND/OR THE PRESCRIBED HEALTHCARE REGIMEN TO THE HEALTHCARE SERVICE PROVIDER 219 the data and/or feedback of OBTAIN DATA FROM THE HEALTHCARE CONSUMER PERIODICALLY RELATED TO THE HEALTHCARE CONSUMER'S CONDITION, AND/OR THE PRESCRIBED HEALTHCARE REGIMEN OPERATION 217 is provided to the healthcare service provider using a network or network system such as network 130 of FIG. 1, and/or any peer-to-peer network, a hybrid peer-to-peer network, a Local Area Network (LAN), a Wide Area Network (WAN), a public network, such as the Internet, a private network, a combination of different network types, or other wireless, wired, and/or a wireless and wired combination network capable of allowing communication between two or more computing systems and/or databases, whether available or known at the time of filing or as later developed.

Returning to FIG. 2, in one embodiment, at PROVIDE THE DATA FROM THE HEALTHCARE CONSUMER RELATED TO THE HEALTHCARE CONSUMER'S CONDITION, AND/OR THE PRESCRIBED HEALTHCARE REGIMEN TO THE HEALTHCARE SERVICE PROVIDER 219 the data and/or feedback of OBTAIN DATA FROM THE HEALTHCARE CONSUMER PERIODICALLY RELATED TO THE HEALTHCARE CONSUMER'S CONDITION, AND/OR THE PRESCRIBED HEALTHCARE REGIMEN OPERATION 217 is provided to the healthcare service provider by storing data representing the information on a database and then providing the healthcare service provider, or other designated party, access to the database. In one embodiment, the database is a data storage device, a designated server system or computing system, or a designated portion of one or more server systems or computing systems, or a distributed database, or an external and/or portable hard drive. In one embodiment, the database is a dedicated mass storage device implemented in software, hardware, or a combination of hardware and software. In one embodiment, the database is a web-based function.

Returning to FIG. 2, in one embodiment, at PROVIDE THE DATA FROM THE HEALTHCARE CONSUMER RELATED TO THE HEALTHCARE CONSUMER'S CONDITION, AND/OR THE PRESCRIBED HEALTHCARE REGIMEN TO THE HEALTHCARE SERVICE PROVIDER 219 the data and/or feedback of OBTAIN DATA FROM THE HEALTHCARE CONSUMER PERIODICALLY RELATED TO THE HEALTHCARE CONSUMER'S CONDITION, AND/OR THE PRESCRIBED HEALTHCARE REGIMEN OPERATION 217 is provided to the healthcare service provider via a computer program product as defined herein.

In one embodiment, at PROVIDE THE DATA FROM THE HEALTHCARE CONSUMER RELATED TO THE HEALTHCARE CONSUMER'S CONDITION, AND/OR THE PRESCRIBED HEALTHCARE REGIMEN TO THE HEALTHCARE SERVICE PROVIDER 219 the data and/or feedback of OBTAIN DATA FROM THE HEALTHCARE CONSUMER PERIODICALLY RELATED TO THE HEALTHCARE CONSUMER'S CONDITION, AND/OR THE PRESCRIBED HEALTHCARE REGIMEN OPERATION 217 is provided to the healthcare service provider via any means, mechanism, method, process, procedure, or device for providing a healthcare consumer information and/or data, whether known at the time of filing or as developed thereafter.

In one embodiment, at PROVIDE THE DATA FROM THE HEALTHCARE CONSUMER RELATED TO THE HEALTHCARE CONSUMER'S CONDITION, AND/OR THE PRESCRIBED HEALTHCARE REGIMEN TO THE HEALTHCARE SERVICE PROVIDER 219 the healthcare consumer is automatically given advice based on, and/or specific to, the data they supply as feedback and the data in the healthcare regimen database, and/or the entered additional information regarding the healthcare consumer, and/or the healthcare consumer's condition, and/or the prescribed healthcare regimen and provided information regarding their prescribed healthcare regimen via e-mail, text message/SMS, phone, or mail.

For instance, in one embodiment, at PROVIDE THE DATA FROM THE HEALTHCARE CONSUMER RELATED TO THE HEALTHCARE CONSUMER'S CONDITION, AND/OR THE PRESCRIBED HEALTHCARE REGIMEN TO THE HEALTHCARE SERVICE PROVIDER 219 if the data supplied by the healthcare consumer indicates that there is an allergic reaction, and/or that the healthcare regimen is ineffective, the healthcare consumer may be automatically advised to contact the healthcare service provider and/or another provider or service, such as a hospital or a 911 service.

In one embodiment, the data and/or feedback provided by multiple healthcare consumers is gathered and used to supplement/improve the healthcare regimen database and/or to generally add to data related to a given prescribed healthcare regimen and/or condition/disease.

In one embodiment, once the data and/or feedback of OBTAIN DATA FROM THE HEALTHCARE CONSUMER PERIODICALLY RELATED TO THE HEALTHCARE CONSUMER'S CONDITION, AND/OR THE PRE- SCRIBED HEALTHCARE REGIMEN OPERATION 217 is provided to the healthcare service provider at PROVIDE THE DATA FROM THE HEALTHCARE CONSUMER RELATED TO THE HEALTHCARE CONSUMER'S CONDITION, AND/OR THE PRESCRIBED HEALTHCARE REGIMEN TO THE HEALTHCARE SERVICE PROVIDER 219, process flow proceeds to EXIT OPERATION 230.

In one embodiment, at EXIT OPERATION 230 process for providing an automated healthcare regimen monitoring and feedback system 200 is exited to await new data.

Using process for providing an automated healthcare regimen monitoring and feedback system 200, a healthcare consumer can be automatically reminded/prompted to comply with a prescribed healthcare regimen, such as when to take a given prescribed dose of medicine, provided periodic information regarding what to expect at various phases of the healthcare regimen, and provided information regarding warning signs of allergic reactions or indications of ineffective healthcare regimen, all without having to directly contact the healthcare service provider. This, in turn, provides the healthcare consumer with a sense of being monitored and advised in an on-going manner through the entire prescribed healthcare regimen.

In addition, using process for providing an automated healthcare regimen monitoring and feedback system 200, the healthcare consumer is also asked to provide specific data related to their experience with the prescribed regimen, often at various specific and/or critical stages of the healthcare regimen, and/or related to specific expected results or potential negative responses, throughout the entire prescribed regimen. Therefore, the healthcare service provider is provided relatively real-time and customized data regarding the healthcare consumer's experience and healing process so the healthcare consumer can more effectively monitor the healthcare consumer's progress. Consequently, using process for providing an automated healthcare regimen monitoring and feedback system 200, healthcare consumers are again benefited by increased monitoring and the healthcare service providers are benefited by receiving more data, and often more relevant data.

In addition, the data gathered by the healthcare service providers from the healthcare service consumers regarding the healthcare service consumers experience as various stages of the prescribed healthcare regime can be used to further refine the expected results data associated with a given healthcare regimen with respect to a given condition. Consequently, using process for providing an automated healthcare regimen monitoring and feedback system 200, the entire population can be benefited by having access to more detailed and accurate data regarding a given healthcare regimen.

As discussed in more detail above, using the above embodiments, with little or no modification and/or healthcare consumer input, there is considerable flexibility, adaptability, and opportunity for customization to meet the specific needs of various healthcare consumers under numerous circumstances.

In the discussion above, certain aspects of one embodiment include process steps and/or operations and/or instructions described herein for illustrative purposes in a particular order and/or grouping. However, the particular order and/or grouping shown and discussed herein are illustrative only and not limiting. Those of skill in the art will recognize that other orders and/or grouping of the process steps and/or operations and/or instructions are possible and, in some embodiments, one or more of the process steps and/or operations and/or instructions discussed above can be combined and/or deleted.

In addition, portions of one or more of the process steps and/or operations and/or instructions can be re-grouped as portions of one or more other of the process steps and/or operations and/or instructions discussed herein. Consequently, the particular order and/or grouping of the process steps and/or operations and/or instructions discussed herein do not limit the scope of the invention as claimed below.

As discussed in more detail above, using the above embodiments, with little or no modification and/or user input, there is considerable flexibility, adaptability, and opportunity for customization to meet the specific needs of various users under numerous circumstances.

The present invention has been described in particular detail with respect to specific possible embodiments. Those of skill in the art will appreciate that the invention may be practiced in other embodiments. For example, the nomenclature used for components, capitalization of component designations and terms, the attributes, data structures, or any other programming or structural aspect is not significant, mandatory, or limiting, and the mechanisms that implement the invention or its features can have various different names, formats, or protocols. Further, the system or functionality of the invention may be implemented via various combinations of software and hardware, as described, or entirely in hardware elements. Also, particular divisions of functionality between the various components described herein are merely exemplary, and not mandatory or significant. Consequently, functions performed by a single component may, in other embodiments, be performed by multiple components, and functions performed by multiple components may, in other embodiments, be performed by a single component.

Some portions of the above description present the features of the present invention in terms of algorithms and symbolic representations of operations, or algorithm-like representations, of operations on information/data. These algorithmic or algorithm-like descriptions and representations are the means used by those of skill in the art to most effectively and efficiently convey the substance of their work to others of skill in the art. These operations, while described functionally or logically, are understood to be implemented by computer programs or computing systems. Furthermore, it has also proven convenient at times to refer to these arrangements of operations as steps or modules or by functional names, without loss of generality.

Unless specifically stated otherwise, as would be apparent from the above discussion, it is appreciated that throughout the above description, discussions utilizing terms such as "obtaining", "linking", "verifying", "monitoring", "browsing", "updating", "associating", "analyzing", "defining", "storing", "saving", "displaying", "implementing", "performing", "creating", "assigning", "estimating", "entering", "modifying", "categorizing", "providing", "processing", "accessing", "selecting", "scheduling", "creating", "using", "comparing", "submitting", "generating", etc., refer to the action and process of a computing system or similar electronic device that manipulates and operates on data represented as physical (electronic) quantities within the computing system memories, resisters, caches or other information storage, transmission or display devices.

Certain aspects of the present invention include process steps or operations and instructions described herein in an algorithmic or algorithmic-like form. It should be noted that the process steps or operations and instructions of the present invention can be embodied in software, firmware, or hardware, and when embodied in software, can be downloaded to reside on and be operated from different platforms used by real time network operating systems.

The present invention also relates to an apparatus or system for performing the operations described herein. This apparatus or system may be specifically constructed for the required purposes, or the apparatus or system can comprise a general purpose system selectively activated or configured/reconfigured by a computer program stored on a computer program product as discussed herein that can be accessed by a computing system or other device.

Those of skill in the art will readily recognize that the algorithms and operations presented herein are not inherently related to any particular computing system, computer architecture, computer or industry standard, or any other specific apparatus. Various general purpose systems may also be used with programs in accordance with the teaching herein, or it may prove more convenient/efficient to construct more specialized apparatuses to perform the required operations described herein. The required structure for a variety of these systems will be apparent to those of skill in the art, along with equivalent variations. In addition, the present invention is not described with reference to any particular programming language and it is appreciated that a variety of programming languages may be used to implement the teachings of the present invention as described herein, and any references to a specific language or languages are provided for illustrative purposes only and for enablement of the contemplated best mode of the invention at the time of filing.

The present invention is well suited to a wide variety of computer network systems operating over numerous topologies. Within this field, the configuration and management of large networks comprise storage devices and computers that are communicatively coupled to similar or dissimilar computers and storage devices over a private network, a LAN, a WAN, a private network, or a public network, such as the Internet.

It should also be noted that the language used in the specification has been principally selected for readability, clarity and instructional purposes, and may not have been selected to delineate or circumscribe the inventive subject matter. Accordingly, the disclosure of the present invention is intended to be illustrative, but not limiting, of the scope of the invention, which is set forth in the claims below.

In addition, the operations shown in the FIG.s, or as discussed herein, are identified using a particular nomenclature for ease of description and understanding, but other nomenclature is often used in the art to identify equivalent operations.

Therefore, numerous variations, whether explicitly provided for by the specification or implied by the specification or not, may be implemented by one of skill in the art in view of this disclosure.

What is claimed is:

1. A computing system implemented process for providing an automated healthcare regimen monitoring and feedback system comprising the following, which when executed by any set of one or more processors configured to perform the process, performs a process comprising:
   providing a healthcare regimen database, the healthcare regimen database at least including data indicating healing process results expected and expected symptoms at various stages of the administration of the healthcare regimen;
   providing a healthcare consumer the ability to participate in the automated healthcare regimen monitoring and feedback system in relation to a healthcare regimen prescribed to the healthcare consumer by a healthcare service provider;
   obtaining contact information from the healthcare consumer associated with a healthcare consumer's preferred method of automatic contact via the automated healthcare regimen monitoring and feedback system;
   using one or more computing systems to link the healthcare consumer, the healthcare consumers contact information, the healthcare regimen prescribed to the healthcare consumer by the healthcare service provider, and at least part of the data in the healthcare regimen database;
   using one or more computing systems to automatically contact the healthcare consumer based, at least in part, on the healthcare regimen prescribed to the healthcare consumer by the healthcare service provider and at least part of the data in the healthcare regimen database to provide the healthcare consumer information regarding the healthcare regimen prescribed to the healthcare consumer by the healthcare service provider, wherein at least a portion of the information provided to the healthcare consumer include at least part of the data indicating healing process results expected at various stages of the administration of the healthcare regimen; and
   using one or more computing systems to obtain data from the healthcare consumer related to the healthcare regimen prescribed to the healthcare consumer by the healthcare service provider based, at least in part, on at least part of the data in the healthcare regimen database and the healthcare regimen prescribed to the healthcare consumer by the healthcare service provider.

2. The computing system implemented process for providing an automated healthcare regimen monitoring and feedback system of claim 1, wherein;
   the healthcare regimen database includes data selected from the group of data consisting of:
   data indicating how often the healthcare regimen is to be administered;
   data indicating potential adverse reactions associated with the prescribed healthcare regimen;
   data indicating symptoms associated with adverse reactions to prescribed healthcare regimen;
   data indicating symptoms associated with various conditions that would require immediate action or indicate another healthcare regimen may be needed; and
   data indicating conditions associated with administering the prescribed healthcare regimen.

3. The computing system implemented process for providing an automated healthcare regimen monitoring and feedback system of claim 1, wherein;
   the healthcare consumer is provided the ability to participate in the automated healthcare regimen monitoring and feedback system in relation to a healthcare regimen prescribed to the healthcare consumer by a healthcare service provider through one or more computing systems using a web-based system.

4. The computing system implemented process for providing an automated healthcare regimen monitoring and feedback system of claim 1, wherein;
   the healthcare consumer's preferred method of automatic contact via the automated healthcare regimen monitoring and feedback system through one or more computing systems is selected form the group of methods of automatic contact consisting of:
   e-mail;
   text message;
   SMS;
   phone;
   mobile application;
   web-page; and
   mail.

5. The computing system implemented process for providing an automated healthcare regimen monitoring and feedback system of claim 1, wherein;
the information or reminders regarding the healthcare regimen prescribed to the healthcare consumer by the healthcare service provider are selected from the group of reminders consisting of:
reminders to administer the prescribed healthcare regimen at about the time the administration is due;
reminders to check one or more vital signs;
reminders to monitor one or more indications of an expected result of the prescribed healthcare regimen on, or about, the timeframe when the result is expected;
reminders to schedule a follow appointment with the healthcare service provider; and
reminders to monitor signs of an adverse reaction to the prescribed healthcare regimen.

6. The computing system implemented process for providing an automated healthcare regimen monitoring and feedback system of claim 1, wherein;
the information or reminders regarding the healthcare regimen prescribed to the healthcare consumer by the healthcare service provider are provided to the healthcare consumer through one or more computing systems using a web-based system.

7. The computing system implemented process for providing an automated healthcare regimen monitoring and feedback system of claim 1, wherein;
the information or reminders regarding the healthcare regimen prescribed to the healthcare consumer by the healthcare service provider are provided to the healthcare consumer through one or more mobile systems.

8. The computing system implemented process for providing an automated healthcare regimen monitoring and feedback system of claim 1, wherein;
the data obtained from the healthcare consumer related to the healthcare regimen prescribed to the healthcare consumer by the healthcare service provider includes data selected from the group of data consisting of:
data indicating compliance with an administration of the prescribed healthcare regimen on, or about, the time the administration of the prescribed healthcare regimen is due;
data regarding the healthcare consumers personal observations regarding the progression of the healthcare regimen; and
data indicating any side effects the healthcare consumer is experiencing at various stages of the healthcare regimen.

9. The computing system implemented process for providing an automated healthcare regimen monitoring and feedback system of claim 1, wherein;
the healthcare consumer is automatically given advice based, at least in part, on the data or feedback the healthcare consumer provides.

10. The computing system implemented process for providing an automated healthcare regimen monitoring and feedback system of claim 1, wherein;
the data or feedback the healthcare consumer provides is used to supplement data in the healthcare regimen database.

11. An automated healthcare regimen monitoring and feedback system comprising:
a healthcare regimen database, the healthcare regimen database at least including data indicating healing process results expected and expected symptoms at various stages of the administration of the healthcare regimen;
one or more computing systems for providing a healthcare consumer the ability to participate in the automated healthcare regimen monitoring and feedback system in relation to a healthcare regimen prescribed to the healthcare consumer by a healthcare service provider;
one or more computing systems for obtaining contact information from the healthcare consumer associated with a healthcare consumer's preferred method of automatic contact via the automated healthcare regimen monitoring and feedback system;
one or more computing systems for linking the healthcare consumer, the healthcare consumers contact information, the healthcare regimen prescribed to the healthcare consumer by the healthcare service provider, and at least part of the data in the healthcare regimen database;
one or more computing systems for automatically contacting the healthcare consumer based, at least in part, on the healthcare regimen prescribed to the healthcare consumer by the healthcare service provider and at least part of the data in the healthcare regimen database to provide the healthcare consumer information regarding the healthcare regimen prescribed to the healthcare consumer by the healthcare service provider, wherein at least a portion of the information provided to the healthcare consumer include at least part of the data indicating healing process results expected at various stages of the administration of the healthcare regimen; and
one or more computing systems for obtaining data from the healthcare consumer related to the healthcare regimen prescribed to the healthcare consumer by the healthcare service provider based, at least in part, on at least part of the data in the healthcare regimen database and the healthcare regimen prescribed to the healthcare consumer by the healthcare service provider.

12. The automated healthcare regimen monitoring and feedback system of claim 11, wherein;
the healthcare regimen database includes data selected from the group of data consisting of:
data indicating how often the healthcare regimen is to be administered;
data indicating potential adverse reactions associated with the prescribed healthcare regimen;
data indicating symptoms associated with adverse reactions to prescribed healthcare regimen;
data indicating symptoms associated with various conditions that would require immediate action or indicate another healthcare regimen may be needed; and
data indicating conditions associated with administering the prescribed healthcare regimen.

13. The automated healthcare regimen monitoring and feedback system of claim 11, wherein;
the healthcare consumer is provided the ability to participate in the automated healthcare regimen monitoring and feedback system in relation to a healthcare regimen prescribed to the healthcare consumer by a healthcare service provider through one or more computing systems using a web-based system.

14. The automated healthcare regimen monitoring and feedback system of claim 11, wherein;
the healthcare consumer's preferred method of automatic contact via the automated healthcare regimen monitoring and feedback system through one or more computing systems is selected form the group of methods of automatic contact consisting of:
e-mail;
text message;
SMS;
phone;
mobile application;
web-page; and
mail.

15. The automated healthcare regimen monitoring and feedback system of claim 11, wherein;

the information or reminders regarding the healthcare regimen prescribed to the healthcare consumer by the healthcare service provider are selected from the group of reminders consisting of:

reminders to administer the prescribed healthcare regimen at about the time the administration is due;

reminders to check one or more vital signs;

reminders to monitor one or more indications of an expected result of the prescribed healthcare regimen on, or about, the timeframe when the result is expected;

reminders to schedule a follow appointment with the healthcare service provider; and reminders to monitor signs of an adverse reaction to the prescribed healthcare regimen.

16. The automated healthcare regimen monitoring and feedback system of claim 11, wherein;

the information or reminders regarding the healthcare regimen prescribed to the healthcare consumer by the healthcare service provider are provided to the healthcare consumer through one or more computing systems using a web-based system.

17. The automated healthcare regimen monitoring and feedback system of claim 11, wherein;

the information or reminders regarding the healthcare regimen prescribed to the healthcare consumer by the healthcare service provider are provided to the healthcare consumer through one or more mobile systems.

18. The automated healthcare regimen monitoring and feedback system of claim 11, wherein;

the data obtained from the healthcare consumer related to the healthcare regimen prescribed to the healthcare consumer by the healthcare service provider includes data selected from the group of data consisting of:

data indicating compliance with an administration of the prescribed healthcare regimen on, or about, the time the administration of the prescribed healthcare regimen is due;

data regarding the healthcare consumers personal observations regarding the progression of the healthcare regimen; and data indicating any side effects the healthcare consumer is experiencing at various stages of the healthcare regimen.

19. The automated healthcare regimen monitoring and feedback system of claim 11, wherein;

the healthcare consumer is automatically given advice based, at least in part, on the data or feedback the healthcare consumer provides.

20. The automated healthcare regimen monitoring and feedback system of claim 11, wherein;

the data or feedback the healthcare consumer provides is used to supplement data in the healthcare regimen database.

\* \* \* \* \*